United States Patent [19]

Cognion et al.

[11] Patent Number: 5,124,495
[45] Date of Patent: Jun. 23, 1992

[54] SELECTIVE HYDROGENOLYSIS OF PERHALOGENATED ETHANE DERIVATIVES

[75] Inventors: Jean-Marie Cognion; Dominique Guillet, both of Saint-Genis-Laval, France

[73] Assignee: Societe Atochem, Puteaux, France

[21] Appl. No.: 627,476

[22] Filed: Dec. 14, 1990

[30] Foreign Application Priority Data

Dec. 15, 1989 [FR] France .................. 89 16643

[51] Int. Cl.$^5$ .................................. C07C 17/10
[52] U.S. Cl. .................................. 570/176
[58] Field of Search .......................... 570/176

[56] References Cited

U.S. PATENT DOCUMENTS 4,910,352 3/1990 Kondo et al.
4,925,998 5/1990 Abraham et al.

FOREIGN PATENT DOCUMENTS 1578933 11/1980 United Kingdom ................ 570/178
2210880 6/1989 United Kingdom
9008748 8/1990 World Int. Prop. O. .......... 570/178

OTHER PUBLICATIONS

Engelhard Catalysts and Precious Metal Chemicals Catalog 1985, pp. 6-7.
Alfa Catalog 1986, European Edition, Research Chemicals and Materials, Catalysts P-205.
Alfa Products, Research Chemicals and Materials 1990-1991, Catalysts P-13.
Hydrodechlorination . . . Over Metal Powder Catalysts and TiO$_2$ Supported Metal and Metal Oxide Catalysts, Chemistry Express, vol. 5, No. 10, pp. 785-788 (1990), Takita et al.
Chemical Abstracts, vol. 112, No. 7, Feb. 12, 1990, p. 685, #54964s.

*Primary Examiner*—Alan Siegel
*Attorney, Agent, or Firm*—Morgan & Finnegan

[57] ABSTRACT

The invention relates to the manufacture of chlorofluoroethanes of formula $CF_3-CHF_xCl_{2-x}$, where x is equal to 0 or 1, by catalytic hydrogenation of a perhaloethane of formula $CF_3-CF_xCl_{3-x}$.

The use of an iridium-based catalyst deposited on a support enables the selectivity to be improved.

9 Claims, No Drawings

SELECTIVE HYDROGENOLYSIS OF PERHALOGENATED ETHANE DERIVATIVES

FIELD OF THE INVENTION

The present invention relates to the manufacture of chlorofluoroethanes of formula:

$$CF_3-CHF_xCl_{2-x} \quad (I)$$

where x is equal to 0 or 1, by catalytic hydrogenation of a perhaloethane of formula:

$$CF_3-CF_xCl_{3-x} \quad (II)$$

The two raw materials, included in the formula (II), are 1,1,1-trichloro-2,2,2-trifluoroethane ($CF_3CCl_3$) and 1,1-dichloro-1,2,2,2-tetrafluoroethane ($CF_3CFCl_2$), in which the substitution of a chlorine atom by a hydrogen atom produces 1,1-dichloro-2,2,2-trifluoroethane ($CF_3CHCl_2$) and 1-chloro-1,2,2,2-tetrafluoroethane ($CF_3CHFCl$) respectively.

BACKGROUND OF THE INVENTION

Catalytic hydrogenation of the compounds (II) has already been described, but the selectivities for the product corresponding to the removal of a single chlorine atom are low. Thus, hydrogenolysis of 1,1-dichloro-1,2,2,2-tetrafluoroethane at 280° C. over a catalyst containing 5% palladium on charcoal (Patent GB 1,578,933) yields a product containing 70% of 1,1,1,2-tetrafluoroethane. Similar results are obtained by C. Gervasutti et al. (Journal of Fluorine Chemistry 1981, 1, 1–20) over a catalyst containing 0.5% of palladium on charcoal: at 170° C. the hydrogenolysis of 1,1-dichloro-1,2,2,2-tetrafluoroethane produces 76% of 1,1,1,2-tetrafluoroethane.

Charcoal-supported metal catalysts containing 0.5% of rhenium, platinum or rhodium (Publications JP 132,536/89, 132,537/89 and 132,538/89 respectively) have also been tested in the hydrogenolysis of 1,1-dichloro-1,2,2,2-tetrafluoroethane; they result in the significant formation of 1,1,1-trifluoroethane, which can attain 30% at 200° C. Furthermore, the complete dechlorination of 1,1-dichloro-1,2,2,2-tetrafluoroethane on bimetallic catalysts based on palladium (Publication JP 172,348/89) or based on platinum (Publications JP 172,349/89 and 128,942/89) has also been described.

To solve the problem of the removal of a single chlorine atom it is necessary to resort, according to Japanese Patent Application 106,051/82 (Publication JP 222,038/83), to a chemical reduction with the zinc-ethanol couple; under the conditions described, the selectivity of the hydrogenolysis of 1,1,1-trichloro-2,2,2-trifluoroethane - to 1,1-dichloro-2,2,2-trifluoroethane attains 90%. However, this process has the disadvantage of employing costly metallic zinc and of giving zinc chloride as a byproduct, which must be destroyed.

Advantageous results have been obtained in the catalytic hydrogenolysis with catalysts containing 0.5% of platinum on alumina or charcoal (Publication JP 149,739/89): at 175° C., with a catalyst on charcoal, 1,1,1-trichloro-2,2,2-trifluoroethane yields a product containing 64% of 1,1-dichloro-2,2,2-trifluoroethane, and at 200° C., with a catalyst on alumina, 1,1-dichloro-1,2,2,2-tetrafluoroethane yields a product containing 42% of 1-chloro-1,2,2,2-tetrafluoroethane.

DESCRIPTION OF THE INVENTION

It is has now been found that the catalytic removal of a single chlorine atom takes place highly selectively if an iridium-based catalyst is employed.

The subject of the present invention is therefore a process for the preparation of chlorofluoroethanes of formula (I) by catalytic hydrogenation of a perhaloethane of formula (II), characterized in that an iridium-based catalyst deposited on a support is employed.

In the catalyst employed according to the invention the iridium content can range from 0.1 to 10% by weight, but is preferably between 0.2 and 8%.

The support may be of very diverse nature and can be chosen, for example, from aluminas, aluminium fluoride and active charcoals. The preferred supports are charcoals which have a specific surface area of between 200 and 1500 m²/g (preferably between 600 and 1200 m²/g), a high porosity (0.3 to 0.7 cm³/g) and a particle size compatible with stationary-bed catalysis (1 to 10 mm). These products are marketed in extrudate or bead form by many companies.

The catalyst according to the invention may be prepared by impregnating the support with an aqueous or organic solution of an iridium derivative, evaporation of the water or of the solvent, and heat treatment at a temperature ranging from 150° to 500° C. (preferably 200° to 400° C.) and under a hydrogen stream (preferably at a pressure of 1 to 5 bars) to liberate the metal. The nature of the iridium derivative employed is of no importance and may be, for example, a chloride, chloroiridic acid or its ammonium salt.

The catalyst according to the invention may also be chosen from commercially available products, for example those of the Engelhard company, which offers catalysts containing from 0.5 to 5% of iridium on aluminas or charcoals.

The catalytic hydrogenation according to the invention may be performed at a temperature ranging from 50° to 300° C., preferably between 150° and 250° C. with a hydrogen/perhaloethane (II) molar ratio ranging from 0.5 to 8 (preferably 1 to 5), at a pressure of 1 to 20 bars (preferably 1 to 5 bars) and an hourly flow rate of 1 to 20 moles of perhaloethane (II) per liter of catalyst.

EXAMPLES

The following examples illustrate the invention without limiting it. In Examples 2 to 8, the results are expressed as the overall degree of conversion ($DC_o$) and the selectivity (S) for a product of the reaction:

$$DC_0 = 100 \times \frac{\text{Number of moles of compound (II) converted}}{\text{Number of moles of compound (II) introduced}}$$

$$S = 100 \times \frac{\text{Number of moles of product formed}}{\text{Number of moles of compound (II) converted}}$$

the analysis at the reactor entry and exit being performed by in-line vapor phase chromatography.

EXAMPLE 1

Preparation of the catalysts

Catalyst A 60 ml (28 g) of an active charcoal which has a porosity of 0.6 cm³/g and a specific surface area of 950 m²/g in the form of extrudates 1.8 mm in diameter are charged into a rotary evaporator. After degassing for 3 hours at 100° C. at reduced pressure (1 kPa), 70 ml of an aqueous solution of iridium trichloride hydrate (53.3% Ir) containing 2.6 g of $IrCl_3$ are introduced and the water is then evaporated off under reduced pressure (1 kPa), followed by drying at 100° C. The product is then treated at 400° C. for 2 hours under a hydrogen stream (10 Nl/h) and a catalyst A containing 5% of iridium is thus obtained.

Catalyst B

By proceding in the same way, but with an aqueous solution containing 0.53 g of $IrCl_3$, a catalyst B containing 1% of iridium is obtained.

Catalyst C

The procedure is the same as for preparing the catalyst B, except that the hydrogen treatment is performed at 200° C. instead of 400° C. The catalyst C thus obtained also contains 1% of iridium.

Catalyst D

The procedure is the same as for preparing the catalyst A, but the active charcoal is replaced with the same volume of an alumina which has a porosity of 0.48 $cm^3/g$ and a specific surface area of 129 $m^2/g$ in the form of 2-mm diameter spheres and an aqueous solution of iridium chloride containing 0.35 g of $IrCl_3$ is employed. A catalyst D containing 0.5% of iridium is thus obtained.

EXAMPLE 2

50 ml of the catalyst A described in Example 1 are introduced into an Inconel tube of 45 cm length and 2.72 cm internal diameter, which is heated electrically, and a mixture of hydrogen and of 1,1-dichloro-1,2,2,2-tetrafluoroethane is then passed through it in the molar ratios and at the flow rates and temperatures shown in the following table, the last part of which collates the results obtained.

TABLE 1

| TEST No. | 1 | 2 | 3 | 4 |
|---|---|---|---|---|
| Operating conditions: | | | | |
| Temperature (°C.) | 100 | 130 | 150 | 200 |
| Molar ratio $H_2/C_2F_4Cl_2$ | 5 | 5 | 5 | 5 |
| $C_2F_4Cl_2$ flow rate (mole/hour) | 0.05 | 0.05 | 0.05 | 0.05 |
| Results | | | | |
| % $DC_0$ of $C_2F_4Cl_2$ | 4 | 42 | 97 | 100 |
| % S for $CF_3CHFCl$ | 86 | 84 | 74 | 50 |
| % S for $CF_3CH_2F$ | 9 | 9 | 13 | 20 |
| % S for $CF_3CH_3$ | 4 | 6 | 13 | 30 |

In most of the cases the selectivity for the hydrogenolysis of a single C—Cl bond is higher than 70%.

By way of comparison, two tests were performed with the catalyst A according to the invention replaced with a catalyst containing 5% of palladium, prepared in the same way and on the same support as in Example 1, with $PdCl_2$ instead of $IrCl_3$. The results, collated in Table 2, which follows, show that with this palladium catalyst the selectivity of the reaction is clearly in favor of the abstraction of two chlorine atoms.

TABLE 2

| COMPARATIVE TEST No. | 5 | 6 |
|---|---|---|
| Operating conditions: | | |
| Temperature (°C.) | 150 | 200 |

TABLE 2-continued

| COMPARATIVE TEST No. | 5 | 6 |
|---|---|---|
| Molar ratio $H_2/C_2F_4Cl_2$ | 4 | 4 |
| $C_2F_4Cl_2$ flow rate (mole/hour) | 0.07 | 0.07 |
| Results | | |
| % $DC_0$ of $C_2F_4Cl_2$ | 100 | 100 |
| % S for $CF_3CHFCl$ | 4 | 3 |
| % S for $CF_3CH_3$ | 1 | 1.2 |
| % S for $CF_3CH_2F$ | 94.5 | 95 |

EXAMPLE 3

In the same apparatus as in Example 2 and with a 25 ml charge of catalyst A, tests of hydrogenolysis of 1,1-dichloro-1,2,2,2-tetrafluoroethane are performed again while the molar ratio $H_2/CF_3CFCl_2$ is decreased.

The operating conditions of the tests and the results obtained are collated in Table 3, which follows.

TABLE 3

| TEST No. | 7 | 8 | 9 |
|---|---|---|---|
| Operating conditions: | | | |
| Temperature (°C.) | 103 | 153 | 200 |
| Molar ratio $H_2/C_2F_4Cl_2$ | 1.5 | 1.5 | 1.5 |
| $C_2F_4Cl_2$ flow rate (mole/hour) | 0.07 | 0.07 | 0.07 |
| Results | | | |
| % $DC_0$ of $C_2F_4Cl_2$ | 26 | 62 | 97 |
| % S for $CF_3CHFCl$ | 88 | 79 | 76 |
| % S for $CF_3CH_3$ | 6 | 12 | 17 |
| % S for $CF_3CH_2F$ | 6 | 7 | 7 |

EXAMPLES 4-7

In the same apparatus as in Example 2 and with a 25 ml charge of catalyst, different tests of hydrogenolysis of 1,1-dichloro-1,2,2,2-tetrafluoroethane were performed, using catalysts B, C and D.

The operating conditions and the results of these tests are collated in Table 4, which follows.

TABLE 4

| EXAMPLE. | 4 | 5 | 6 | 7 |
|---|---|---|---|---|
| Operating conditions: | | | | |
| Catalyst | B | C | C | D |
| Temperature (°C.) | 150 | 150 | 190 | 230 |
| Molar ratio $H_2/C_2F_4Cl_2$ | 4.5 | 5 | 5 | 1.5 |
| $C_2F_4Cl_2$ flow rate (mole/hour) | 0.03 | 0.05 | 0.05 | 0.07 |
| Results | | | | |
| % $DC_0$ of $C_2F_4Cl_2$ | 55 | 59 | 83 | 97 |
| % S for $CF_3CHFCl$ | 81 | 90 | 92 | 76 |
| % S for $CF_3CH_3$ | 11 | 6 | 4 | 14 |
| % S for $CF_3CH_2F$ | 8 | 4 | 4 | 6 |

EXAMPLE 8

50 ml of a new charge of catalyst A is introduced into the same apparatus as in Example 2 and used to perform the hydrogenation of 1,1,1-trichloro-2,2,2-trifluoroethane ($CF_3$—$CCl_3$).

The operating conditions of the test and the results obtained are collated in Table 5, which follows. Besides the expected product, 1,1-dichloro-2,2,2-trifluoroethane ($CF_3CHCl_2$), the byproduct formed is chiefly 1,1,1-trifluoroethane ($CF_3CH_3$) and 1-chloro-2,2,2-trifluoroethane ($CF_3CH_2Cl$).

TABLE 5

| Operating conditions: | |
|---|---|
| Temperature (°C.) | 160 |
| Molar ratio $H_2/C_2F_3Cl_3$ | 1.5 |

TABLE 5-continued

| | |
|---|---|
| $C_2F_3Cl_3$ flow rate (mole/hour) | 0.06 |
| Results | |
| % $DC_0$ of $C_2F_3Cl_3$ | 68 |
| % S for $CF_3CHFCl_2$ | 81 |
| % S for $CF_3CH_3$ | 8 |
| % S for $CF_3CH_2Cl$ | 3 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for the preparation of chlorofluoroethanes of formula:

$$CF_3-CHF_xCl_{2-x} \quad (I)$$

where x is equal to 0 or 1, comprising catalytic hydrogenation with hydrogen of a perhaloethane of formula:

$$CF_3-CF_xCl_{3-x} \quad (II)$$

at a temperature of between 50° and 300° C. and at a pressure of 1 to 20 bars, characterized in that the catalyst consists of iridium deposited on a support of alumina, aluminum fluoride or active charcoal, the iridium content of said catalyst ranging from 0.1 to 10% by weight.

2. Process according to claim 1, wherein the support is an active charcoal which has a specific surface are of between 200 and 1500 m²/g, a porosity of 0.3 to 0.7 cm³/g and a particle size of 1 to 10 mm.

3. Process according to claim 1, wherein the hydrogen/perhaloethane (II) molar ratio is between 0.5 and 8.

4. Process according to claim 1, wherein the hourly flow rate of perhaloethane (II) is from 1 to 20 moles per liter of catalyst.

5. Process according to claim 1, wherein the iridium content is between 0.2 and 8%.

6. Process according to claim 2, wherein the specific area is between 600 and 1200 m²/g.

7. Process according to claim 1, wherein the hydrogenation temperature is between 150° and 250° C.

8. Process according to claim 1, wherein the pressure is between 1 and 5 bars.

9. Process according to claim 3, wherein the molar ratio is between 1 and 5.

* * * * *

UNITED STATES PATENT AND TRADEMARK OFFICE
CERTIFICATE OF CORRECTION

PATENT NO. : 5,124,495

DATED : June 23, 1992

INVENTOR(S) : Jean-Marie COGNION and Dominique GUILETT

It is certified that error appears in the above-identified patent and that said Letters Patent is hereby corrected as shown below:

In Column 5, Table 5-continued, change "% S for $CF_3CHFCl_2$" to --% S for $CF_3CHCl_2$--.

Signed and Sealed this

Second Day of November, 1993

*Attest:*

BRUCE LEHMAN

*Attesting Officer*       Commissioner of Patents and Trademarks